(12) United States Patent
Jordan Navas et al.

(10) Patent No.: US 11,647,994 B2
(45) Date of Patent: May 16, 2023

(54) SYSTEM FOR THE STORAGE AND TRACEABILITY OF BIOLOGICAL SPECIMEN HOLDERS

(71) Applicant: DREAMPATH DIAGNOSTICS, Strasbourg (FR)

(72) Inventors: Pablo Jordan Navas, Madrid (ES); Thomas Crepieux, Strasbourg (FR); Valerie Wilhelm, Eschau (FR); Thomas Hirtz, Bosselshausen (FR)

(73) Assignee: DREAMPATH DIAGNOSTICS, Strasbourg (FR)

( * ) Notice: Subject to any disclaimer, the term of this patent is extended or adjusted under 35 U.S.C. 154(b) by 344 days.

(21) Appl. No.: 16/865,177

(22) Filed: May 1, 2020

(65) Prior Publication Data
US 2020/0345333 A1 Nov. 5, 2020

(30) Foreign Application Priority Data
May 2, 2019 (FR) ..................................... 19 04636

(51) Int. Cl.
*A61B 10/00* (2006.01)
*G01N 1/00* (2006.01)
*G01N 35/00* (2006.01)
*B01L 9/00* (2006.01)

(52) U.S. Cl.
CPC ............ *A61B 10/0096* (2013.01); *B01L 9/52* (2013.01); *G01N 1/00* (2013.01); *G01N 35/00732* (2013.01); *B01L 2300/021* (2013.01); *G01N 2001/002* (2013.01); *G01N 2035/00801* (2013.01)

(58) Field of Classification Search
CPC ................. A61B 10/0096; G01N 1/00; G01N 35/00732; G01N 2001/002; G01N 2035/00089; G01N 2035/00801; B01L 9/52; B01L 2300/021
See application file for complete search history.

(56) References Cited

U.S. PATENT DOCUMENTS

| | | | | |
|---|---|---|---|---|
| 3,746,161 A * | 7/1973 | Jones | ....................... | B65D 1/36 206/804 |
| 6,118,582 A * | 9/2000 | Del Buono | ......... | B01L 3/50855 359/398 |
| 8,662,392 B2 * | 3/2014 | Hagen | ................... | B01L 3/5453 235/375 |
| 2021/0260592 A1 * | 8/2021 | Hughes | .................. | G06K 17/00 |

FOREIGN PATENT DOCUMENTS

| | | | |
|---|---|---|---|
| FR | 3055559 A1 | 3/2018 | |
| FR | 3063659 A1 | 9/2018 | |

* cited by examiner

*Primary Examiner* — Justin N Olamit
(74) *Attorney, Agent, or Firm* — Craft Chu PLLC; Andrew W. Chu

(57) ABSTRACT

The device for the storage and traceability of biological specimens placed in holders is provided with identification information in the form of encoded data. The device includes at least one tray provided with a plurality of cells for the storage of the holders provided with storage housings for the holders, at least one apparatus for reading encoded data and determining data relative to the location of each holder within the receptacle, and a computerized processor for the data read and determined by the apparatus. The is a device for recognizing an empty housing within the receptacle defined by a detector for a physical characteristic of the bottom of the cell or an element secured to this bottom.

7 Claims, 4 Drawing Sheets

SYSTEM FOR THE STORAGE AND TRACEABILITY OF BIOLOGICAL SPECIMEN HOLDERS

CROSS-REFERENCE TO RELATED APPLICATIONS

See Application Data Sheet.

STATEMENT REGARDING FEDERALLY SPONSORED RESEARCH OR DEVELOPMENT

Not applicable.

THE NAMES OF PARTIES TO A JOINT RESEARCH AGREEMENT

Not applicable.

INCORPORATION-BY-REFERENCE OF MATERIAL SUBMITTED ON A COMPACT DISC OR AS A TEXT FILE VIA THE OFFICE ELECTRONIC FILING SYSTEM (EFS-WEB)

Not applicable.

STATEMENT REGARDING PRIOR DISCLOSURES BY THE INVENTOR OR A JOINT INVENTOR

Not applicable.

BACKGROUND OF THE INVENTION

1. Field of the Invention

The present invention relates to a system for the storage and traceability of biological specimens placed in holders provided with identification information in the form of encoded data, said system including:
  at least one receptacle provided with storage housings for said holders, said receptacle being defined by a tray having a plurality of cells forming said housings, configured each to house a biological specimen holder, delimited by a bottom topped by a peripheral wall,
  at least one apparatus for reading encoded data and determining data relative to the location of each holder within the receptacle, including at least one cavity configured to accommodate the receptacle on a temporary basis, as well as
  means for computerized processing of the data read and determined by said apparatus. The present invention is intended for the medical field in the analysis of tissue and cell samples.

2. Description of Related Art Including Information Disclosed Under 37 CFR 1.97 and 37 CFR 1.98

In the context of the medical care of a patient or of research work in the human, animal or plant fields, tissue or cell samples are commonly taken for histological and/or molecular analysis, which may or may not be intended to prepare a diagnosis.

In order to allow perfect viewing under the microscope of the cell or tissue structures being analyzed, such samples are subject to prior preparation including different steps. In short, during the latter, the fresh sampled specimens are placed in open cassettes, undergoing a dehydration phase, then inclusion in paraffin, leading to blocks of biological specimens. Fine and regular cuts, taken from the latter, are next placed on slides, undergo various treatments intended to dye the structural elements to be observed, and are lastly covered with a resin, then a strip allowing them to be read under the microscope and providing them with protection.

All of these preparatory steps of the biological samples for analysis thereof assume many manipulations, during which measures must be taken to ensure traceability.

The same is true during analysis phases, during which the sampled slides must travel from one station to another within a same laboratory, or between different laboratories, or between different pathologists, etc.

Likewise, during storage and warehousing operations of the blocks or slides of biological specimens, in particular for any subsequent comparative analyses, archiving and traceability solutions must be implemented.

Equipment intended to carry out traceability measures in the field of biological samples are already commercially available, and in particular described in publication FR 3,055,559 by this applicant, or publication EP 3,200,118.

BRIEF SUMMARY OF THE INVENTION

The aim of the present invention is to propose a more effective alternative solution, making it possible to improve the productivity of all of the personnel who may be involved during the preparation, analysis and storage phases of tissue or cell samples. Another aim of the invention is to propose a solution making it possible to facilitate the handling of the biological specimen holders, defined by the cassettes, the paraffin blocks and the slides, and to preserve the structural integrity throughout the entire process that they undergo, in particular in the case of slides.

To that end, the present invention relates to a system of the type indicated in the preamble, characterized in that it includes means for recognizing an empty housing within said receptacle, defined by means for detecting a physical characteristic of the bottom of the cell or an element secured to this bottom.

Such a characteristic has the advantage of allowing a configuration of the computer processing means, at the end of which the latter deliver information indicating that a given housing is empty to an operator responsible for archiving biological specimens. The operator can then deduce from this information that the absence of detection of encoded data in this same given housing is not due to a reading error by the apparatus, but simply an absence of biological specimen holder. It can also be provided to configure the computer processing means such that they do not provide the operator with any information regarding the emptiness of a housing, and that an alert is only delivered in case of observation, by the computer processing means, both of the presence of a holder in a housing and an absence of reading of the corresponding encoded data.

In other words, the subject matter of the invention allows the operator to dedicate his time to correcting any reading errors actually committed by the reading apparatus, and therefore to prevent him from performing needless verification tasks, observed during the implementation of certain equipment of the prior art. In short, owing to such a characteristic, the effectiveness and therefore the productivity of operators are improved.

According to a conceivable variant embodiment of the system according to the invention, it has been imagined that the bottom of the cell can for example include at least one volume extending in relief or in a hollow on its face designed to receive the biological specimen holder, while the apparatus is equipped with detection means of said volume, mounted in said cavity.

Another solution proposed in the context of the invention provides that the apparatus can be equipped with a gray level sensor mounted in said cavity, configured to recognize a gray level representative of an empty cell.

With the same aim, according to still another alternative, the bottom of each cell can include information representative of its emptiness, in the form of encoded data.

With an aim of preserving the structural integrity of a biological specimen slide, it has been provided, in a case in which each cell is designed to house, by nesting, a biological specimen holder having a rectangular parallelepiped slide shape, that each cell preferably has a depth, comprised between the upper edge of its peripheral wall and its bottom, at least equal to the thickness of a slide.

Furthermore, in order to facilitate the handling of the biological specimens, it has been provided that, in such a variant embodiment, the bottom of the cell has a planar central segment extended by two end segments, at least one of which is curved so as to arrange at least one zone with play, extending below a plane passing through the central segment and delimited by the peripheral wall and the bottom of the cell.

Additionally, according to one preferred feature of the invention, the bottom is planar over a length equal to ⅔ of the length of a cell.

The curved end segment then advantageously has a curve radius such that it allows tilting of a slide housed in the cell bearing tangentially along the curved end segment, so as to limit the risk of breaking of a slide as much as possible during its removal by an operator.

According to one additional feature of the device according to the invention, means designed to be able to guarantee a total insertion of the receptacle into said cavity before the implementation of the apparatus for reading encoded data and determining location data can be provided.

The latter can for example be defined by an optical fork, the reading apparatus of which is equipped, and which is designed to be able to detect a pair of orifices arranged on an edge of the tray.

Furthermore, it has also been imagined for the reading apparatus to be able to be equipped with means for identifying the type of receptacle inserted into said cavity. The advantage is then the ability to impart a universal nature to the apparatus making it possible to limit the number of equipment items to be acquired by the research and analysis laboratories to manage their stock of biological specimens.

BRIEF DESCRIPTION OF THE SEVERAL VIEWS OF THE DRAWINGS

The present invention will be better understood upon reading the description done in reference to the appended figures, provided as non-limiting examples.

DETAILED DESCRIPTION OF THE INVENTION

Figure 1:
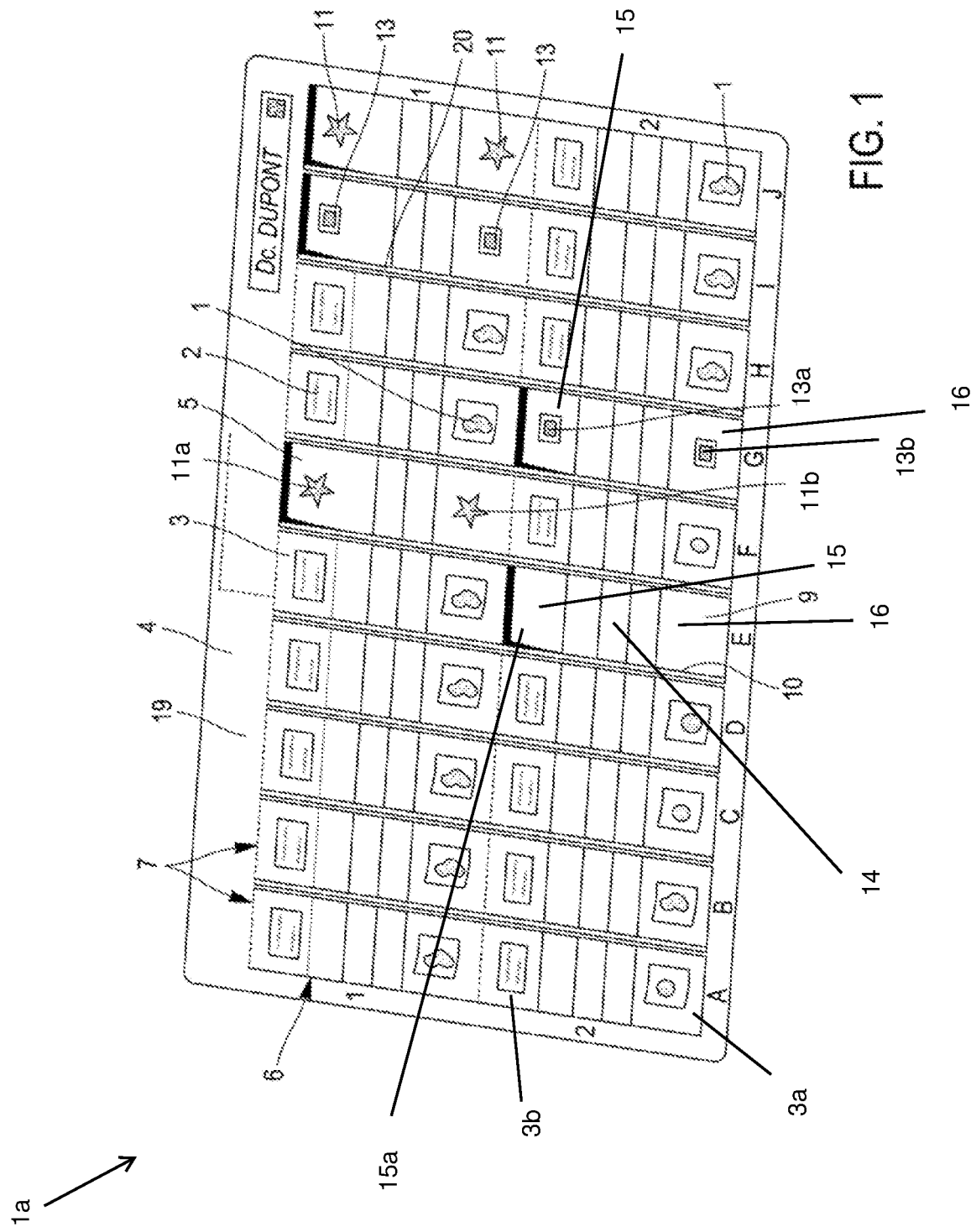
FIG. 1 illustrates a top view of a tray defining an embodiment variant of the receptacle according to the invention, including a plurality of solid cells of biological specimens slides and several empty cells.
Figure 2:
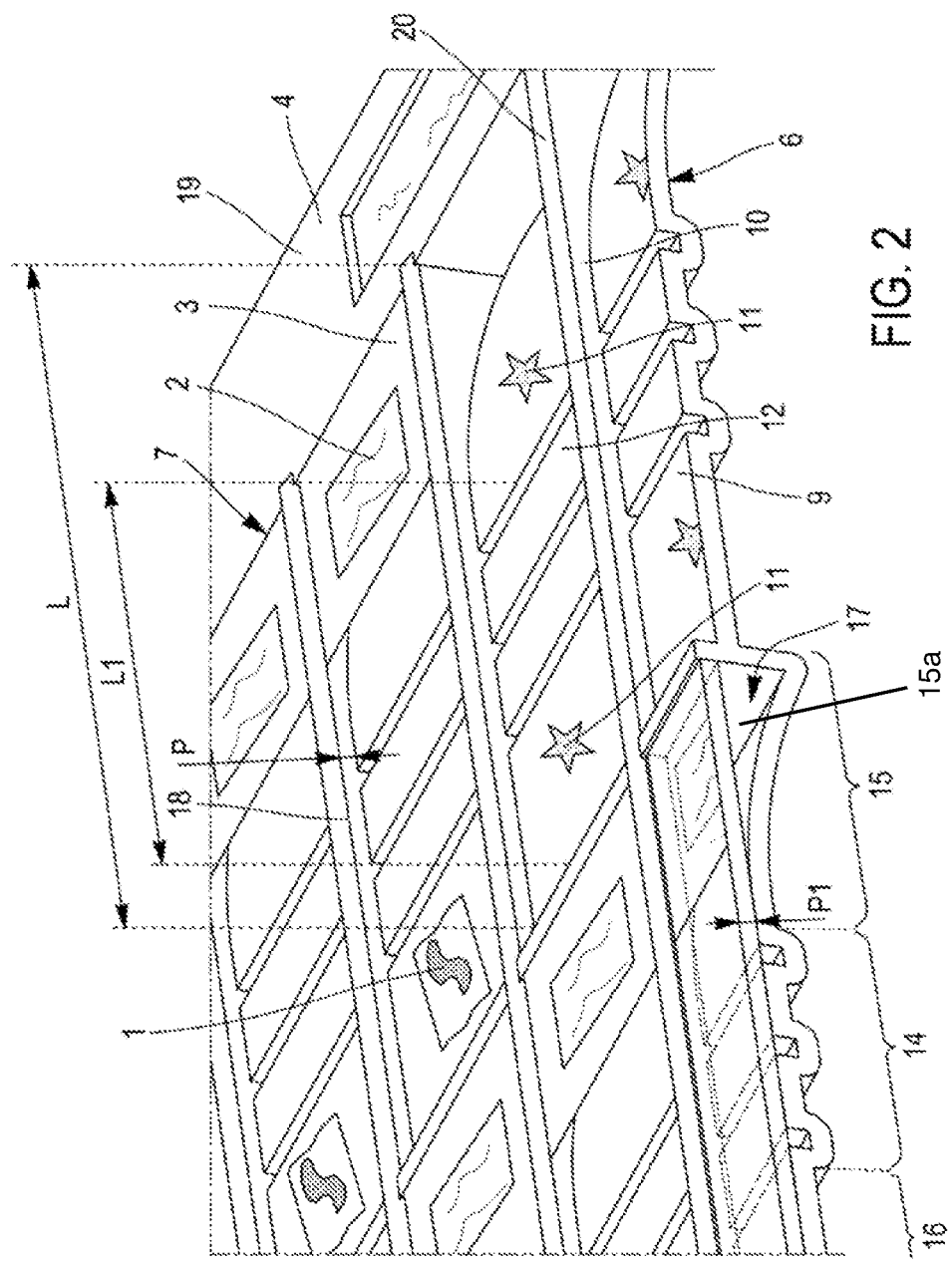
FIG. 2 shows a cross-sectional view of the tray of FIG. 1.

As indicated above, the present invention relates to a system for the storage and traceability of biological specimens 1 sampled from a patient, an animal, or even a plant, for medical research or analysis work.

The following disclosure relates to the application of such a system 1 a to the traceability of biological specimens 1 provided with identification information in the form of encoded data 2, during their analysis phase in a pathology department, during which they are conveyed on slides 3 having a specimen end 3a and an encoded data end 3b, conventionally of rectangular parallelepiped shape, stored in tray-forming receptacles 4 having a plurality of cells 5 organized in columns 6 and rows 7. However, it is clear that the system according to the invention is studied to be suitable for all of the steps of the lifetime of such biological specimens 1, from their collection to their destruction.

Conventionally, the system according to the invention includes at least one apparatus (not illustrated) including at least one cavity configured to temporarily accommodate a receptacle, such as a tray 4. The system is configured for a means for reading encoded data 2 and determining data relative to the location of each slide 3 within the tray 4. In the case at hand, in the illustrated example, the latter correspond to the locations in terms of columns 6 and rows 7 occupied by the cells 5 in which the slides 3 are housed on the tray 4. More specifically, in this example, the tray 4 contains fifteen slides 3 of biological specimens 1, while the cells 5 occupying rows F, I, J of the column 1 and those occupying rows E and G of column 2 are empty.

Furthermore, the system according to the invention is also configured for a computer processing means (not shown) for the data read and determined by the apparatus or means for reading encoded data.

According to the invention, the system is a means for recognizing an empty housing within said receptacle, and therefore an empty cell 5 within the tray 4.

In reference to the figures, the cells 5 are designed to be able to house each slide 3 by nesting and are delimited by a bottom 9 topped by a peripheral wall 10. In order to allow the reading apparatus to recognize an empty cell 5, there is a secured element 11, 13, (a first secured element 11a, 13a, a second secured element 11b, 13b) on the bottom 9. The system is configured for the means for reading encoded data, such as a means for detecting a physical characteristic of the bottom 9 of a cell 5 or of an element 11, 13 secured to this bottom 9, which can be provided in the context of the invention.

Thus, according to one conceivable variant embodiment, the bottom 9 of a cell 5 can include two volumes 11 (a first secured element 11a, a second secured element 11b), for example star-shaped, extending in relief or hollow on its face 12 designed to receive the slide 3 bearing the biological specimen 1, the reading apparatus then being equipped with means for detecting said volume, mounted in said receiving cavity on the tray 3.

According to one alternative solution, the bottom 9 of each cell 5 can include information representative of its emptiness, for example in the form of encoded data 13, printed on discs affixed on the bottom 9 or printed directly on the bottom 9, and able to be read by the encoded data reading means included by the reading apparatus. A character detector of the "OCR" (optical character recognition) type could also be provided, able to conclude on an absence of slide 3, if characters are detected printed directly on the bottom 9 or on labels adhered thereon (not illustrated).

It should be noted that in these examples, the volumes 11, encoded data 13 or printed characters are implanted on the bottom 9 of the cells 5 so as to be hidden, on the one hand by the encoded data 2 and on the other hand by the biological specimen 1 included by the slides 3, when they are in the cells 5 (cf. FIG. 1). Thus, the volumes 11, encoded data 13 or printed characters are only detected in case of empty cells 5 and their detection is therefore immediately interpreted by the computer processing means as being representative of such an empty cell 5.

One additional solution proposed by the present invention in order to allow the recognition by the reading apparatus of an empty cell 5 consists of equipping the latter with a gray level sensor mounted in the receiving cavity of the tray 4, and configured to recognize a gray level representative of an empty cell 5, by defining different gray levels detected in case of presence of a slide 3. In practice, to that end, the camera with which the reading apparatus, which conventionally includes the device according to the invention, is equipped, will be used. Thus, the computer processing means of the latter will be configured to compare the gray levels of an image of a tray 4 containing slides 3 read by the camera, with the gray levels of a control image read beforehand by this same camera while the tray 4 was empty. A match between the gray levels of a cell 5 of the control image and the gray levels of a cell 5 of a tray 4 being read being synonymous with an absence of slide in this same cell, no reading error information will be delivered, which makes it possible to free the operator from a verification step. In short, such a verification will only prove necessary in the case where the computer processing means identify both a read error of the encoded data 2 and an absence of match between the gray levels of a cell 5 of the control image and the gray levels of a cell 5 of a tray 4 being read, indicating the presence of a slide 3.

In the tray 4 illustrated in the figures, each cell 5 has a depth p, comprised between the upper edge 18 of its peripheral wall 18 and the face 12 of the central segment 14 of the bottom 9, at least equal to the thickness p1 of a slide 3 of biological specimen 1. Thus, when such a slide 3 is housed in a cell 5, it has no zone emerging outside the latter, capable of being exposed to any untimely impacts or scraping that risk damaging it. Such a feature therefore makes it possible to ensure the structural integrity of the slides 3 housed in the cells 5.

In order to improve the gripping of a slide 3 housed in a cell 5, the bottom 9 of the cell 5 has further been designed so as to have a planar central segment 14 extended by two end segments 15, 16, the end segment 16 of which is also planar, while the curved end segment 15 is curved so as to arrange at least one zone 15a with play 17, extending below the plane passing through the central segment 14 and delimited by the peripheral wall 10 and the bottom 9 of the cell 5. The first secured element 11a, 13a is placed on the curved end segment 15 of each cell. The second secured element 11b, 13b placed on said end segment 16 of each cell.

Figure 3:
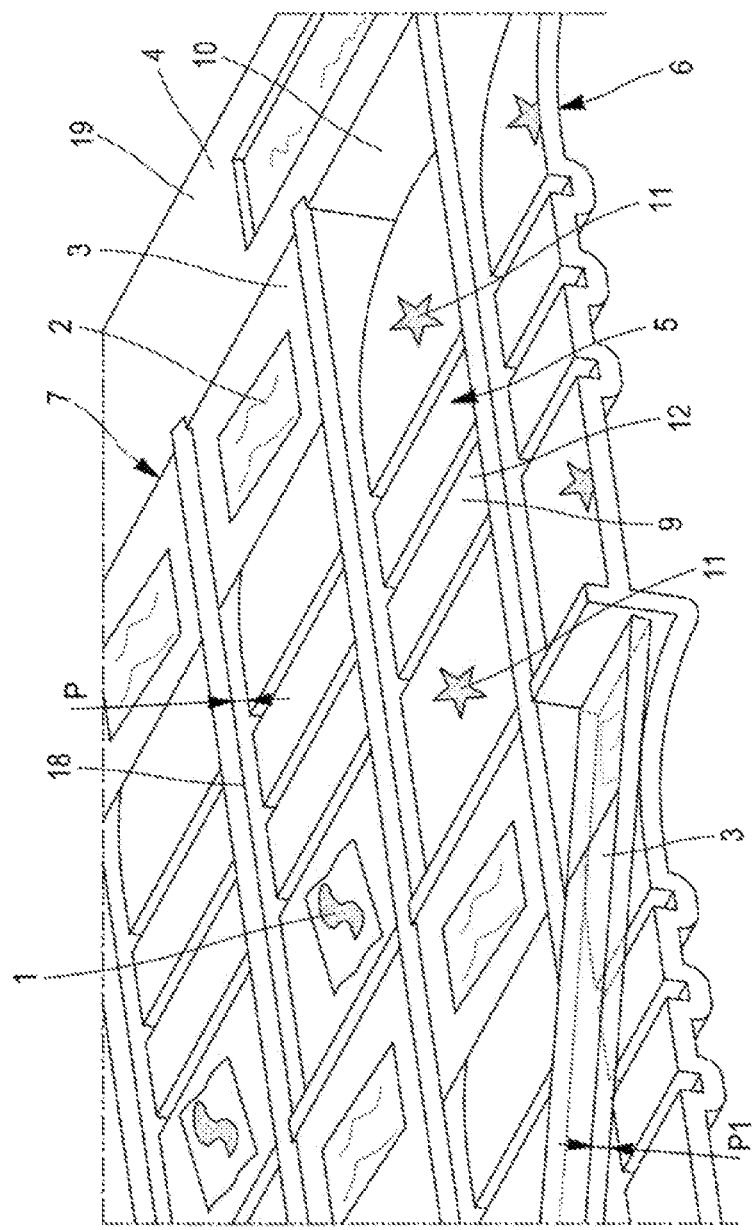
FIG. 3 is a cross-sectional view of the tray of FIG. 1 illustrating the removal of a sampled slide.

Additionally, in order to guarantee that when idle, a slide 3 housed in a cell 5 remains flat, the end segments 16 and the central segment 14 extend together over a length L1 equal to ⅔ of the length L of the cell 5. Any risk of breaking of a slide 3 during its removal, related to an overly abrupt movement is avoided owing to the fact that the curved end segment 15 preferably has a curve radius allowing a tilting of a slide housed in the cell bearing tangentially along the curved end segment (cf. FIG. 3). Of course, a structure can also be considered in which the bottom of each cell is only planar along its central segment, while both of its end segments are curved. In this case, the gripping of a slide is further optimized because it can be done indifferently by either of its ends, with the same level of gentleness.

Figure 4:
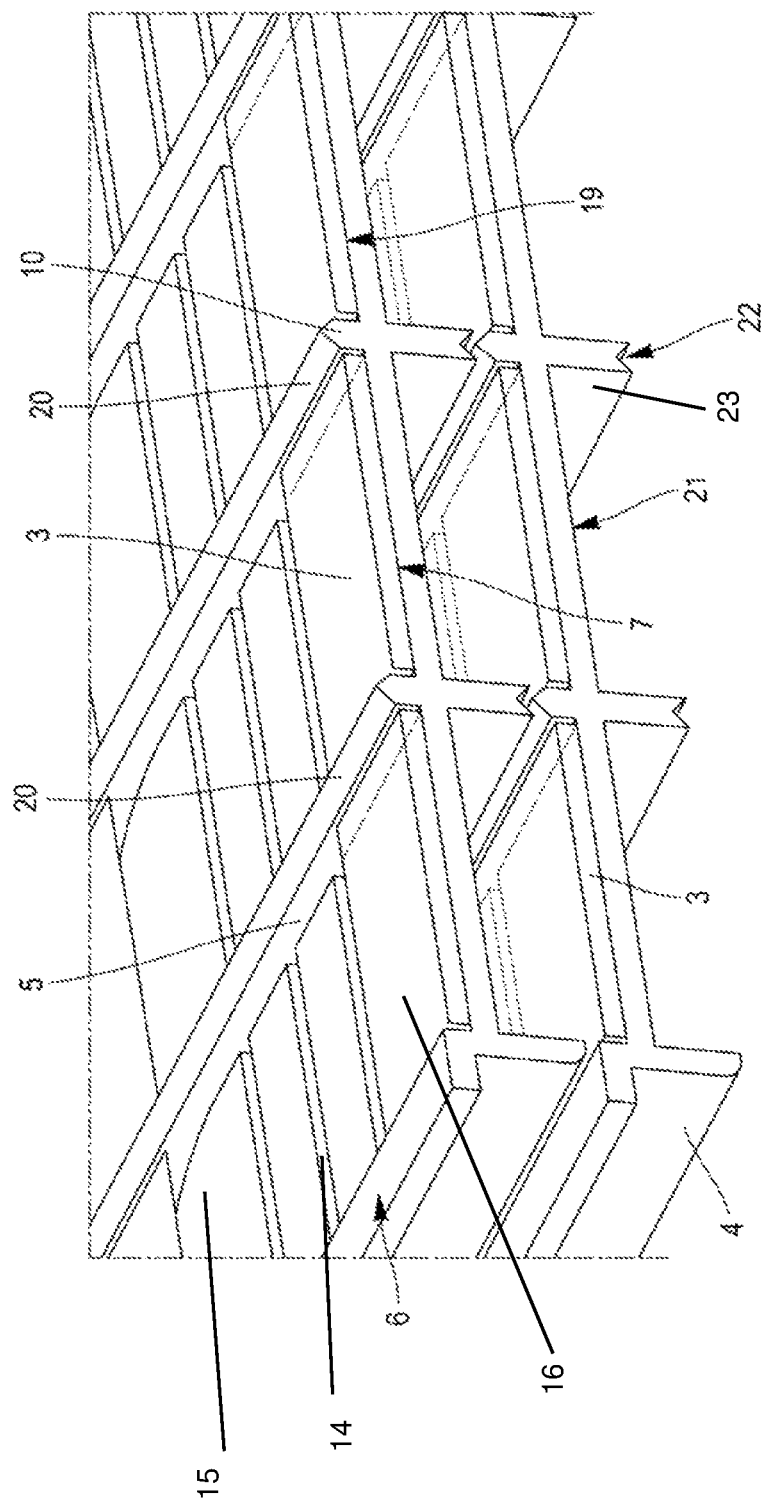
FIG. 4 is a longitudinal sectional view of two trays of FIG. 1, superimposed.

As illustrated in FIG. 4, the tray 4 is advantageously molded so as to be able to be stacked easily with an identical tray 4. To that end, in the illustrated variant embodiment, its upper face 19 includes a plurality of ribs 20 of triangular section, formed along each row 7 in the extension of the peripheral wall 10 of each cell 5, while its lower face 21 includes a plurality of grooves 22 of "V"-shaped section complementary to that of the ribs 20, and extending parallel thereto, along tabs 23 extending the lower face 21. Such a feature allows better organization within biological analysis laboratories and optimization of the space available for the storage and warehousing of the slides 3 while ensuring the protection thereof.

It should further be noted that the device according to the present invention is preferably completed by means designed to be able to guarantee a total insertion of a receptacle such as the tray 4 into the cavity that it includes, before the implementation of its means for reading encoded data 2 13 [sic] and determining location data, the nature of which has been specified above.

To that end, the reading apparatus can for example be equipped with an optical fork designed to be able to detect a pair of orifices (not illustrated) arranged on an edge of the tray 4.

Furthermore, the reading apparatus to be able to be equipped with means for identifying the type of receptacle inserted into said cavity, so as to cause the commissioning, if applicable, of reading means dedicated to a given type of receptacle.

We claim:

1. A system for storage and tracing biological specimens, the system comprising:
    a tray being comprised of a plurality of cells,
    wherein each cell is comprised of a bottom and a peripheral wall above said bottom, and
    wherein said bottom is comprised of an end segment, a planar central segment, and a curved end segment, said planar central segment being between said end segment and said curved end segment so as to define a zone below said planar central segment;
    a first secured element placed on said curved end segment of each cell;
    a second secured element placed on said end segment of each cell; and
    a slide being comprised of a specimen end and an encoded data end opposite said specimen end, a biological specimen being placed on said specimen end, encoded data being placed on said encoded data end, said slide being removably placed in at least one cell of said plurality of cells so as to cover said second secured element with said biological specimen and said first secured element with said encoded data when said slide is within a respective cell,
    wherein said encoded data end is moveable within said zone so as to be tiltable into said zone during removal from said at least one cell of said plurality of cells.

2. The system for storage and tracing, according to claim 1, wherein said first secured element is comprised of at least one of a group consisting of a shaped volume on said curved end segment and encoded data on said curved end segment, and wherein said second secured element is comprised of at least one of a group consisting of a shaped volume on said end segment and encoded data on said end segment.

3. The system for storage and tracing, according to claim 2, wherein said shaped volume extends downward from a surface of said curved end segment.

4. The system for storage and tracing, according to claim 1, wherein said slide has a slide depth.

5. The system for storage and tracing, according to claim 4, wherein each cell has a cell depth from said bottom to an upper edge of said peripheral wall, said cell depth being at least equal to said slide depth.

6. The system for storage and tracing, according to claim 1, wherein said slide is rectangular.

7. The system for storage and tracing, according to claim 1, wherein said bottom has a bottom length, said planar central segment being two thirds length of said bottom length.

* * * * *